(12) United States Patent
Iketaki

(10) Patent No.: US 6,633,432 B2
(45) Date of Patent: Oct. 14, 2003

(54) OPTICAL DEVICE AND A MICROSCOPE

(75) Inventor: Yoshinori Iketaki, Oume (JP)

(73) Assignee: Olympus Optical Co., Ltd., Tokyo (JP)

( * ) Notice: Subject to any disclaimer, the term of this patent is extended or adjusted under 35 U.S.C. 154(b) by 102 days.

(21) Appl. No.: 09/934,440

(22) Filed: Aug. 21, 2001

(65) Prior Publication Data

US 2002/0141052 A1 Oct. 3, 2002

(30) Foreign Application Priority Data

Aug. 21, 2000 (JP) ........................................ 2000-249320

(51) Int. Cl.⁷ .............................................. G02B 21/26
(52) U.S. Cl. ...................... 359/386; 359/387; 359/388; 359/389
(58) Field of Search ................................ 359/386, 387, 359/388, 389, 390, 385, 370, 371; 356/310, 330, 326

(56) References Cited

U.S. PATENT DOCUMENTS

| 4,917,462 A | * | 4/1990 | Lewis et al. ................ 359/368 |
| 5,739,040 A | * | 4/1998 | Ishikawa .................... 436/172 |
| 6,128,077 A | * | 10/2000 | Jovin et al. ................. 356/310 |

FOREIGN PATENT DOCUMENTS

| JP | 08-184552 | 7/1996 |
| JP | 10-142151 | 5/1998 |

OTHER PUBLICATIONS

Yasuo Ozakawa, Masaaki Fujii and Mitsuo Ito: "Direct Observation of Second Excited $^{1,3}(n,\Pi^*)$ States of Pyrazine by UV–IR Double Resonance Dip Spectroscopy", Chemical Physics Letters, vol. 171, No. 4, Aug. 10, 1990, pp. 341–346.

Terry M. Turpin et al: "ImSyn™: Optoelectronic Product for Image Synethesis and Correlation", SPIE, vol. 3073, No. 0277, pp. 178–184, 1997.

Ohmsha, Ltd., New Generation Engineering Series "Laser Engineering", 1999, edited by Sadao Nakai, and English language translation thereof.

* cited by examiner

Primary Examiner—Mohammad Sikder
(74) Attorney, Agent, or Firm—Frishauf, Holtz, Goodman & Chick, P.C.

(57) ABSTRACT

An optical device and microscope of simple construction are provided that are capable of readily attaining super resolution with good focusing performance. This comprises a light source means (2, 3, 4, 6, 8) that generates light of multiple different wavelengths, a light condensation means to focus lights of these multiple wavelengths on an object 1, and an emitted light detector means 17 for detection of light emitted from said object 1. Among said multiple lights of different wavelengths generated from said light source means, at least one light forms a condensed light pattern of multiple spatial modes. These multiple lights are condensed upon said object 1 such that part of the region of the condensed light pattern of said multiple spatial modes is made to spatially overlap with the condensed light pattern of the other light.

10 Claims, 15 Drawing Sheets mode pattern of pump light after transmission through phase plate mode pattern of erase light after passage through phase plate

US 6,633,432 B2

OPTICAL DEVICE AND A MICROSCOPE

BACKGROUND OF THE INVENTION

1. Field of the Invention

The present invention relates to an optical device and microscope. In particular, the present invention relates to a microscope-spectrometer device, such as a super-resolution fluorescence microscope using light of two different wavelengths, that improves detection sensitivity and spatial resolution by concentrating light at a sample surface using the wavefronts of light of two wavelengths.

2. Description of the Related Art

Technology of optical microscopy has long been developed, resulting in the invention of various types of microscopes. Moreover, microscope systems with improved performance have been developed in recent years due to advances in related technologies beginning with laser technology and electron imaging technology.

Within this context, for example, Publication of Unexamined Patent Application No. Hei 8-184552 has proposed a high performance microscope capable of chemical analysis, in addition to control of contrast of the obtained image, by the use of a double-resonance absorption process resulting from illumination of the sample by light of multiple wavelengths.

The principles of this microscope, which operates by selection of a particular molecule by use of a double-resonance absorption process to observe absorption and fluorescence due to particular optical transitions, will be explained while referring to FIG. 9–FIG. 17. FIG. 9 shows the electron structure of a valence electron orbital of a molecule comprising the sample. First an electron of a valence electron orbital of a molecule in a ground state (S0) as indicated in FIG. 9 is excited by light into an excited state (S1 state) as shown in FIG. 10. Then light of another wavelength causes excitation in the same manner, resulting in a second excited state (S2 state) shown in FIG. 11. The molecule returns to the ground state indicated by FIG. 12 after light emission by fluorescence or phosphorescence.

Microscopy utilizing double-resonance absorption observes an absorption image and an emitted light image using the absorption processes of FIG. 10 and the fluorescence or phosphorescence process of FIG. 11. Although this microscopy method first excites a molecule comprising the sample into the S1 state as shown in FIG. 10 by light of a resonant wavelength $\lambda 1$ due to laser light, etc., the number of molecules in the S1 state per unit volume increases with the intensity of the irradiating light.

Here the line absorption coefficient is given by the product of the absorption cross section per molecule and the number of molecules per unit volume. Then the line absorption coefficient with respect to illuminating resonant wavelength $\lambda 2$ during the process of FIG. 11 depends upon the intensity of light of the initial irradiating wavelength $\lambda 1$. That is to say, the absorption coefficient with respect to $\lambda 2$ becomes controllable by the intensity of light of $\lambda 1$. This indicates that transmission image contrast can be entirely controlled by light of wavelength $\lambda 1$ if the sample is irradiated with light of the two wavelengths, wavelength $\lambda 1$ and wavelength $\lambda 2$, and if the transmission image due to wavelength $\lambda 2$ is imaged.

Moreover, if de-excitation is possible from the excited state of FIG. 1 by fluorescence or phosphorescence, the intensity of such light emission is proportional to the number of molecules in the S1 state. Therefore it becomes possible to control image contrast even during use as a fluorescence microscope.

Furthermore, microscopy using double-resonance absorption is capable of chemical analysis and isn't simply limited to the above mentioned control of image contrast. That is to say, the outermost valence electron orbital shown in FIG. 9 has inherent energy levels for each molecule. Therefore wavelength $\lambda 1$ depends upon the molecule, and simultaneously, $\lambda 2$ also is characteristic of the molecule.

Here, although it is possible to observe an absorption or fluorescence image to a certain extent even when irradiation occurs at the conventional single wavelength, such observation is generally impossible until precise analysis is carried out of the chemical composition of the sample since wavelength regions coincide for any number of molecular absorption bands.

In contrast, since a microscopy using double-resonance absorption is limited to molecules emitting light or absorbing light at the two wavelengths $\lambda 1$ and $\lambda 2$, it becomes possible to determine chemical composition of the sample with greater accuracy than by the conventional method. Moreover, since absorption is intense when a valence electron is excited only for light that has an electrical field vector along the polarization direction of wavelength $\lambda 1$ and wavelength $\lambda 2$, it becomes possible to even analyze the orientation direction of the same molecule if polarization direction of wavelength $\lambda 1$ and wavelength $\lambda 2$ are determined and then an absorption or a fluorescence image is taken.

Moreover, recently (e.g., Publication of Unexamined Patent Application No. Hei 10-142151) a fluorescence microscope has been proposed that has high spatial resolution that exceeds the diffraction limit by use of double-resonance absorption. FIG. 13 is a conceptual drawing showing the process of double-resonance absorption that occurs in a molecule. The molecule in the ground state S0 is excited to S1, which is a first excited state, due to light at wavelength $\lambda 1$. Furthermore, this shows excitation to S2, which is a second excited state, due to light at wavelength $\lambda 2$. This also shows the case of extremely weak fluorescence from S2.

Extremely interesting phenomena occur in the case of a molecule that has the optical properties indicated in FIG. 13. FIG. 14 is a conceptual drawing of the double-resonance absorption process, in the same manner as FIG. 13, wherein the horizontal X axis indicates width of spatial distance, spatial region A1 is irradiated by light of wavelength $\lambda 2$, and spatial region A0 isn't irradiated by light of wavelength $\lambda 2$.

Within FIG. 14, numerous molecules are generated in the S1 state due to excitation by light of wavelength $\lambda 1$ at spatial region A0, and then fluorescence is visible due to light emission at wavelength $\lambda 3$ from spatial region A0. However, since spatial region A1 is irradiated by light of wavelength $\lambda 2$, most molecules in the S1 state are immediately excited to the high S2 state such that molecules in the S1 state aren't present. This type of phenomenon is confirmed for any number of molecules. By this means, even if fluorescence of wavelength $\lambda 3$ entirely disappears, fluorescence itself at the A1 region becomes entirely controllable since there was no fluorescence originally from the S2 state. Therefore fluorescence occurs only in the A0 spatial region.

This result has extremely important meaning when considered from the standpoint of the applied field of microscopy. That is to say, a conventional scanning-type laser microscope, etc. concentrates light into a micro-beam by means of a condensing lens and then scans across the observed sample. During this process, micro-beam size becomes that of the diffraction limit determined by wavelength and the numerical aperture of the condensing lens, and spatial resolution better than this limit can't be anticipated.

However, in the case of FIG. 14, lights of two types (wavelength $\lambda 1$ and wavelength $\lambda 2$) are skillfully combined spatially, and the fluorescence region is controlled by irradiation of light of wavelength $\lambda 2$. Therefore, for example, upon consideration of the region of irradiation of light of wavelength $\lambda 1$, the fluorescence region can be made more narrow than even that of the diffraction limit determined by wavelength and numerical aperture of the condensing lens. Therefore this principle can be utilized to make possible a super-resolution microscope (e.g. a fluorescence microscope) using double-resonance absorption to exceed the diffraction limit.

Furthermore, the inventors of the present invention have already also proposed a novel invention for increasing super-resolution of a microscope. That is to say, a fluorescence labeler molecule (in order to sufficiently utilize performance of a super-resolution microscope) and irradiation timing, etc. of the sample with light of two wavelengths $\lambda 1$ and $\lambda 2$ are proposed. This proposed irradiation of a sample for which a biological molecule is chemically bonded via biochemical dyeing technology to a fluorescent probe molecule which is dyed with various types of molecules having at least three quantum states including the ground state and for which thermal equilibration is more strongly controlling than equilibration resulting from fluorescence transition during de-excitation back to the ground state from an energy state other than the first excited state; wherein fluorescence from the S1 state is controlled by immediate excitation to a higher quantum level by light of wavelength $\lambda 2$ after the dyed molecule has been excited to the S1 state by light of wavelength $\lambda 1$. Optical properties of molecules can be utilized in this manner to improve spatial resolution by artificial control of the fluorescence spatial region.

Optical properties of such a molecule can be explained from the standpoint of quantum chemistry. That is to say, generally molecules are comprised of various atoms bounded by $\pi$ or $\sigma$ bonds. In other words, molecular orbitals of a molecule exist as $\pi$ molecular orbitals or a molecular orbitals, and electrons present in these molecular orbitals take on the important role of bonded the various atoms. Among such molecular orbitals, electrons of a molecular orbitals strongly bond the various atoms and determine inter-atomic distances within the molecule that form the skeleton of the molecule. In contrast, an electron in a it molecular orbital contributes almost nothing to bonding of the various atoms and instead restrains the entire molecule with an extremely weak force.

In many cases, when light excites an electron in a molecular orbital, inter-atomic spacing of the molecule changes greatly, and large structural changes occur which include dissociation of the molecule. As a result, kinetic energy of the atoms and energy imparted to the molecule by light are mostly changed into thermal energy due to structural change. Therefore excitation energy isn't consumed in the form of the light called fluorescence. Moreover, even if fluorescence were assumed to occur during this process, the duration of such fluorescence would be extremely short since structural change of a molecule is extremely fast (shorter than a p-sec).

In contrast, an electron in a $\pi$ orbital has the property of excitation with nearly no effect upon molecular structure itself, staying for a long time period in an excited quantum state of high quantum position, and subsequent decaying by emission of fluorescence on the order of a n-sec.

According to quantum chemistry, possession of a $\pi$ molecular orbital by a molecule is equivalent to possession of a double bond so that an essential condition for selection of the utilized fluorescent labeler molecule becomes the possession of abundant double bonds. However, even among molecules having double bonds, six member rings such as benzene and pyridine have been confirmed to have extremely weak fluorescence from the S2 excited state (e.g., M. Fuji, et al., Chem. Phys. Lett. 171 (1990) 341).

Therefore if a molecule having six member rings, such as benzene, pyridine, etc., is selected as a fluorescence labeler molecule, the lifetime of fluorescence from the S1 state would be long, and fluorescence from the molecule would be readily controlled by excitation from the S1 state to the S2 state by photo-activation. Therefore effective use becomes possible for super-resolution. That is to say, if observation is carried out after dyeing by such a fluorescence labeler molecule, not only does it become possible to observe a fluorescent image of the sample at high spatial resolution, but it also is possible to selectively dye only particular chemical structures of the biological sample, and it becomes possible to analyze even the detailed chemical structures of the sample.

Moreover, since double-resonance absorption generally only occurs when particular conditions are satisfied, such as polarization state and wavelengths of the two light wavelengths, these conditions can be utilized to learn the structure of the molecule in extremely fine detail. That is to say, the double-resonance absorption process occurs strongly when there is a strong correlation between polarization direction of the light and orientation direction of the molecule, and when the molecular orientation direction has a particular angle relative to respective polarization directions of the lights of the two wavelengths. Therefore the extent that fluorescence disappears can be varied by irradiating the sample simultaneously with light of two wavelengths and then rotating polarization direction of each respective light. Therefore from such variation, spatial orientation information can be obtained for the tissue under observation. This is also possible by adjustment of the two wavelengths of light.

As explained above per previous proposals of the inventors of the present invention, it is understood that this has high analytical performance in addition to super-resolution. Furthermore, by use of timing of the two wavelengths of light, wavelength $\lambda 1$ and $\lambda 2$, it becomes possible to improve signal-to-noise ratio, to effectively control fluorescence, and to more effectively attain super-resolution.

FIG. 15 shows an example of the construction of a super-resolution microscope according to the above mentioned previous proposals of the inventors of the present invention. This super-resolution microscope splits laser light from a Nd:YAG laser by a half mirror 52. One beam passes through third harmonics generator 53 and is made to enter dichroic mirror 54. The other beam passes through mirror 55, Raman shifter 56, mirror 57 and phase plate 58, and then is made to enter dichroic mirror 54. Laser light from triple-wave generator 53 and laser light passing through phase plate 58 are spatially combined at dichroic mirror 54. This combined laser light passes through a condenser lens 59, pinhole 60, dichroic mirror 61, and objective lens 62 and then is concentrated upon a sample 65 held by a cover glass 64 upon a mobile stage 63. Moreover, the phase plate 58, as shown by FIG. 16, is formed so as to impart a phase shift π at positions that are point-wise symmetric with respect to the optical axis. Sample 65 has been dyed beforehand with a fluorescent labeler molecule.

Moreover, fluorescent light emitted from sample 65 passes through objective lens 62, is split from the return route by dichroic mirror 61, passes through pinhole 66, sharp cut filter 67, band sharp cut filter 68, and notch filter 69, and then is received by photomultiplier 70. Furthermore, a sharp cut filter 67, a band pass filter 68, a notch filter 69, and photomultiplier 70 are contained within a light-shielded box 71, and pinhole 66 is formed in this light-shielded box 71.

Laser light from third harmonics generator 53 of the super-resolution microscope shown in FIG. 15 as pump light causes excitation from the S0 state to the S1 state of the fluorescent labeler molecule, and laser light from Raman shifter 56 exciting to the S2 state from the S1 state as erase light is made into an annular beam by phase plate 58 and is spatially combined with pump light at dichroic mirror 54, thereby suppressing fluorescence outside of the vicinity of the optical axis where intensity of the erase light upon sample 65 becomes zero. Only those fluorescent labeler molecules present in a region effectively narrower than the extent of the pump light are observed in the super-resolution image.

However, according to various types of investigations by the inventors of the present invention, it was found that the above mentioned various types of super-resolution microscopes have points requiring further improvement with respect image formation. For example, the super-resolution microscope shown in FIG. 15 spatially combines pump light with erase light made annular by passage through phase plate 58 shown in FIG. 16, thereby suppressing fluorescence outside the vicinity of the optical axis where intensity of erase light becomes zero upon sample 65. However, it is difficult to actually make intensity of the central region of the erase light entirely zero.

The reason for this is that phase plate 58 can not be manufactured in the ideal manner called for by design values. Therefore a phase differential of π can't be imparted at positions that are point-wise symmetric with respect to the beam optical axis, and electrical field intensity can't be entirely nulled. Therefore among light waves at positions that are point-wise symmetric with respect to the beam optical axis, a non-nulled component remains upon the optical axis, and a non-nulled component accumulates upon the optical axis with respect a light wave of a component of 2π total azimuthal angle centered upon the beam optical axis, thereby generating an electrical field intensity which can't be ignored even at the beam central axis as shown in FIG. 17.

Therefore under such conditions, even when pump light and erase light are made to overlap upon the sample surface and super-resolution is attempted using fluorescence control phenomena, the intensity of fluorescence at the central part of the pump light declines, resulting in severe adverse effects due to a worsening of super-resolution and a drop of the total amount of fluorescent signal.

BRIEF SUMMARY OF THE INVENTION

The object of the present invention, in consideration of such earlier problems, is to solve such deficiencies.

The object of the present invention is to provide an optical device and microscope of simple construction that is capable of readily obtaining super-resolution with good focusing performance.

In order to attain the above mentioned object, a microscope of the present invention includes an optical device having a light source for generating multiple lights of different wavelengths, a focusing optical device that focuses said multiple lights at an object and an emitted light detector for detecting light given off from said object. The microscope is constructed such that at least one light among the multiple lights of different wavelength generated by said light source is light formed as a condensed light pattern of multiple spatial modes, and such that these multiple lights are condensed upon said object by said focusing optical device such that only a partial region of said multi-spatial mode pattern spatially overlaps a condensed light pattern of the other light.

Moreover, the present invention is a microscope for observation of a sample that is dyed by a molecule having at least three electron states including a ground state and characterized as having a first light source for generation of a first light of a wavelength λ1 which causes a transition of said molecule from the ground state to a first excited state, a second light source for generation of second light of a wavelength λ2 which causes a transition of said molecule from a first excited state to a second excited state of higher energy level, a condensed light optical system for focusing of said first light and second light upon said sample, and an emitted light detector for detection of light emitted from said molecule; the microscope being characterized in that the microscope is constructed such that light of said first light from said first light source is generated to form a multi-spatial mode condensation pattern and such that said condensed light optical system makes just a portion of the region of said condensed light pattern of the first light spatially overlap said condensed light pattern of the second light.

For the microscope of the present invention, said first light source and second light source made to be coherent light sources.

Moreover, for the microscope of the present invention, the microscope has a phase distribution generation element that causes the wavefront of said first light of wavelength λ1 to have a phase distribution.

Furthermore, for the microscope of the present invention, said phase distribution generation element has a multiplicity of divided regions for which the wavefront has a phase differential of either zero or π.

Moreover, for the microscope of the present invention, said divided region has a phase differential of π with respect to an adjacent region.

Furthermore, for the microscope of the present invention, said second light also has a multi-spatial mode condensed light pattern.

That is to say, the present invention divides spatially condensed beam patterns of pump light and/or erase light into multiple regions of multiple modes, partially overlaps spatially these beams upon the sample condensed light surface, suppresses fluorescence from a divided region of a first part of pump light, and therefore makes possible detection of a fluorescent signal from a minute region of smaller size than the diffraction limit of the pump light.

Generally when a light beam that has a wavefront, such as a laser light source, is passed through a phase filter that has a two-dimensional phase distribution, a condensed beam is formed that has arbitrary spatial modes. This technology has been previously applied in the field of optical information technology (e.g., T. M. Turpin, et al., Proc. SPIE, 3073 (1997) 178–184).

For example, as shown in FIG. 1, pump light is divided into two parts as multiple modes within the condensed light beam. In the same manner, erase light is also divided into two parts. When these two beams are made to overlap only at one divided region, fluorescence from that part is entirely suppressed, resulting in a multi-fold improvement of resolution.

Moreover, there also is a triple-division method as shown in FIG. 2, and spatial resolution also can be improved by generation of high-order modes. Furthermore, as shown in FIG. 3, a method of removal of fluorescence is also possible wherein pump light is formed that has two-dimensional higher order spatial modes such that the spatial pattern of erase light forms a ring shape, a single divided region remains of spatially divided pump light, and the region external thereto is made to overlap with the irradiation region of erase light.

In this manner, multiple methods are possible since spatial division into multiple regions by making a condensed light beam pattern of pump light or erase light that has multiple modes utilizes existing technology and is basically capable of carrying out wavefront scanning by the use of coherent light that has matched wavefronts.

One such method that may be used utilizes a phase plate, as shown in FIG. 1–FIG. 3, to place regions appropriately within the laser wavefront of either 0 or π phase differential within a plane perpendicular to the optical axis. Moreover, if the pump light is partitioned into two parts, the aperture plane may be is divided left-right into two regions such that phase differentials of pump light or erase light differ from one another by π. If a beam of such light is then condensed, the sign of electrical field intensity reverses at the boundary interface of the two regions, resulting in an electrical field of zero, and resulting in a condensed light beam with a shape that has two peaks. In the same manner, if the aperture plane is divided into three regions such that phase differentials of adjacent regions differ by π, the condensed light beam takes on a shape that has three peaks as indicated by FIG. 2.

Furthermore, methods are possible for imparting the above mentioned phase differentials, such as evaporating-depositing an optically thin film of high refractive index (e.g., magnesium fluoride) upon an optically polished glass substrate, direct chemical etching of a glass substrate, etc. In addition, it is also possible to utilize the laser light source itself to generate a multi-spatial mode beam. That is to say, by selection of boundary conditions of the laser oscillator, it is possible to cause oscillation of a light of a mode pattern that has n×m multiple peaks; wherein n is the number of peaks along the height direction in the beam cross section, and m is the number of peaks in the width direction in the beam cross section. This is the so-called TEM mode. FIG. 4(a), (b), and (c) show three representative low-order TEM mode patterns (Ohmsha, Ltd., New Generation Engineering Series, "Laser Engineering", 1999, edited by Sadao NAKAI). If the laser itself is used to generate a multi-spatial mode beam in this manner, it becomes possible to attain super resolution without use of a phase plate, and construction of a compact microscope system becomes possible.

The present invention in this manner can obtain an optical device and microscope of simple construction that can readily attain super resolution with good focusing performance since, among a multiplicity of lights of different wavelengths, at least one light forms a condensed light pattern of multiple spatial modes, and since these multiple lights are made to focus on an object such that only part of the region of the multi-spatial mode condensed light pattern overlaps spatially with the condensed light pattern of other light.

DETAILED DESCRIPTION

A working example of a microscope and optical device according to this invention will be explained below while referring to FIG. 5–FIG. 8.

Figure 1:
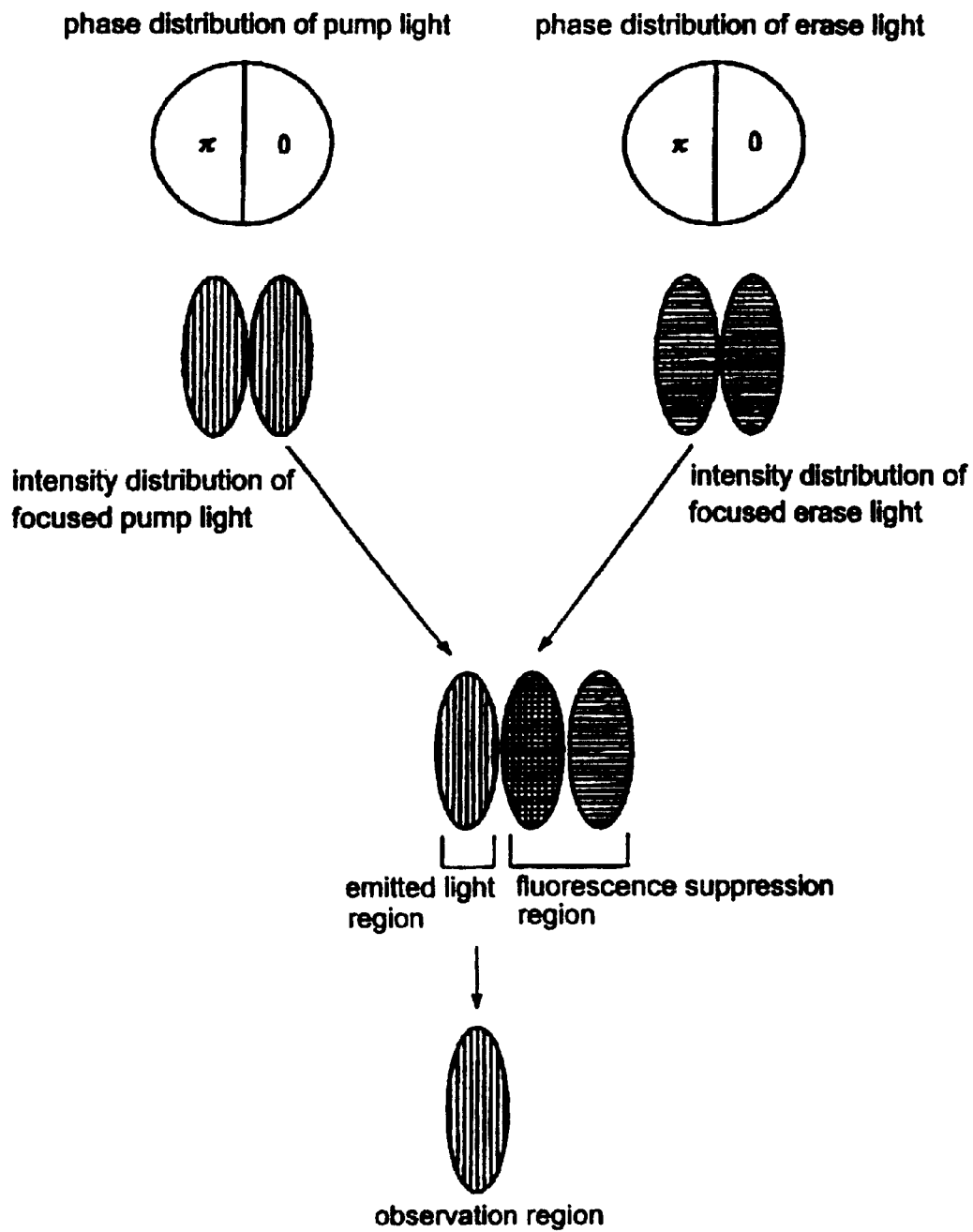
FIG. 1 is an explanatory drawing for explanation of principles of the present invention.
Figure 2:
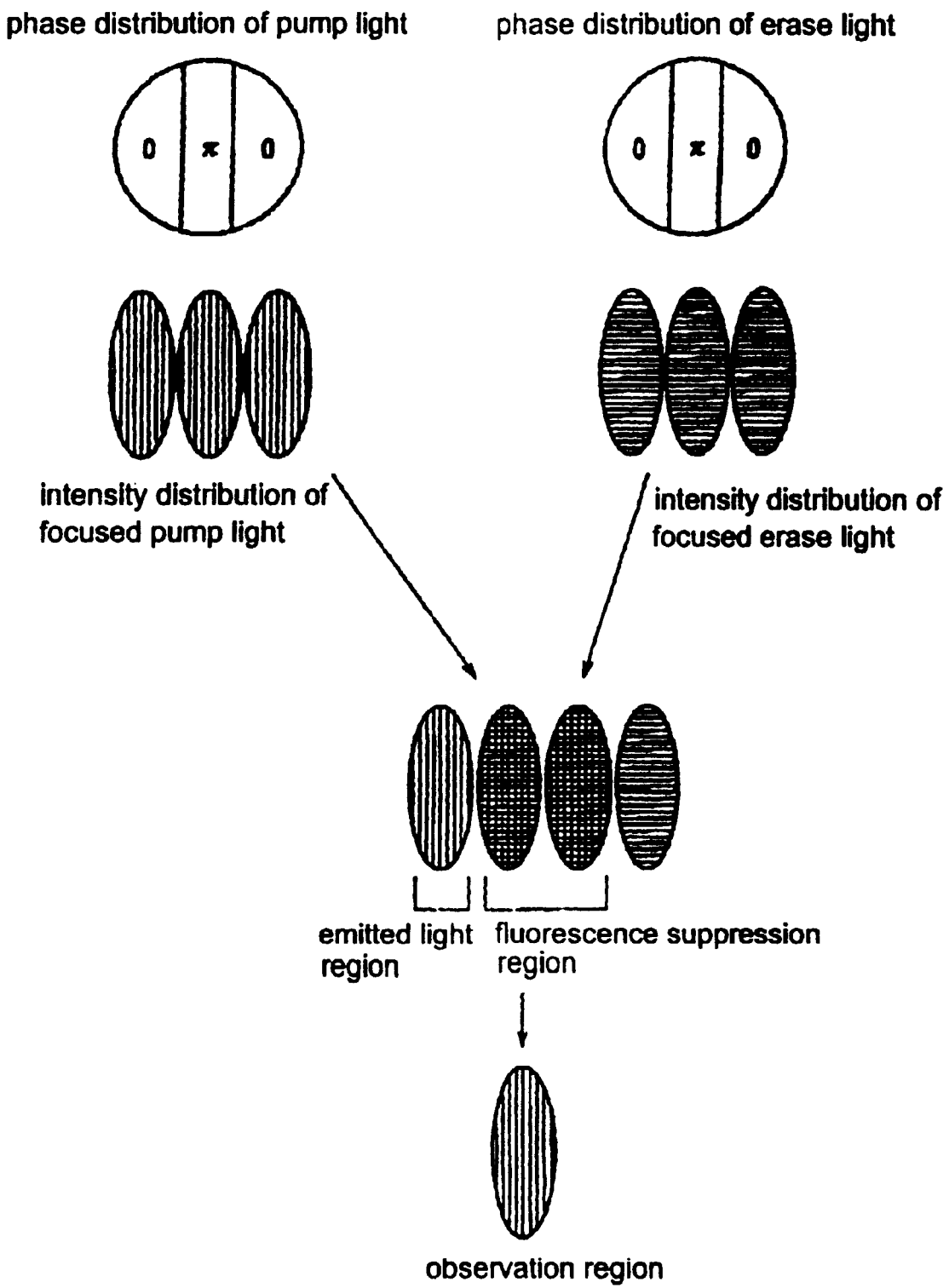
FIG. 2 in the same manner is an explanatory drawing for explanation of principles of the present invention.
Figure 3:
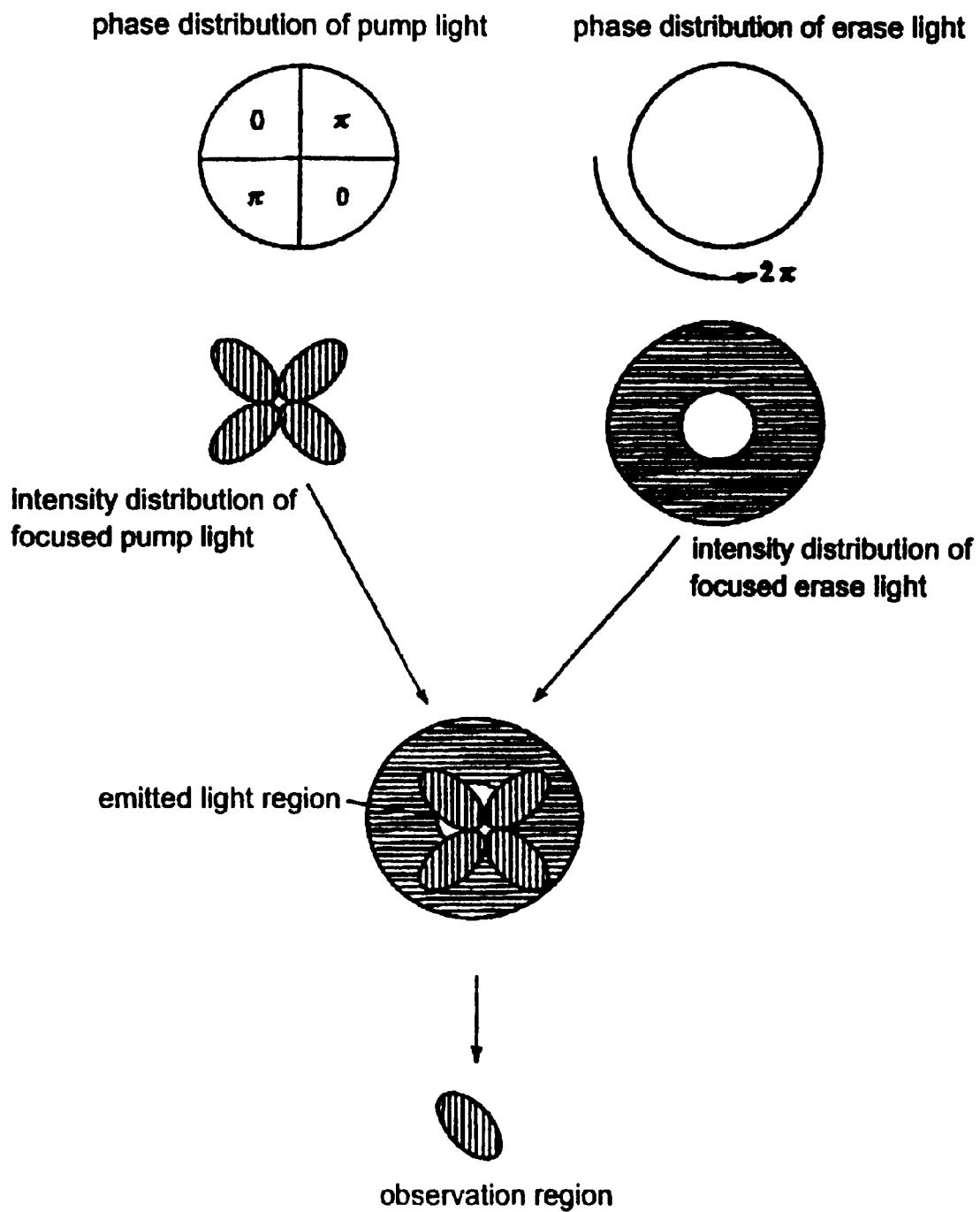
FIG. 3 in the same manner is an explanatory drawing for explanation of principles of the present invention.
Figure 4:
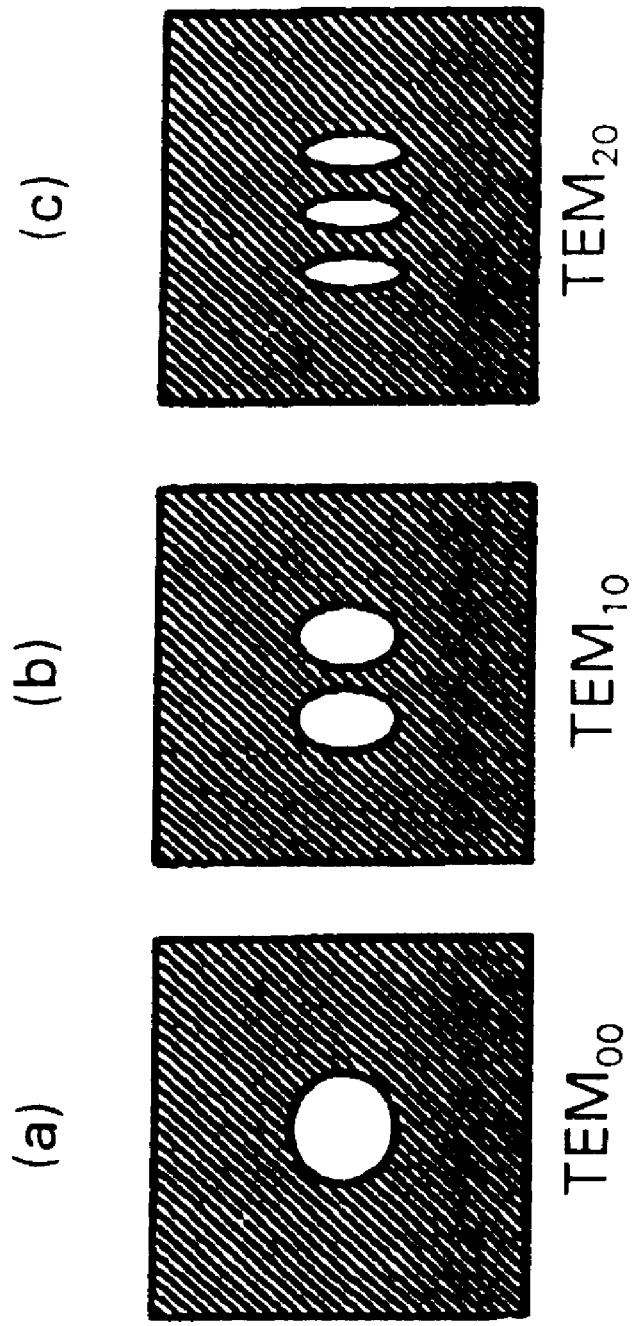
FIG. 4 is an explanatory drawing showing three representative low-order TEM mode patterns.
Figure 5:
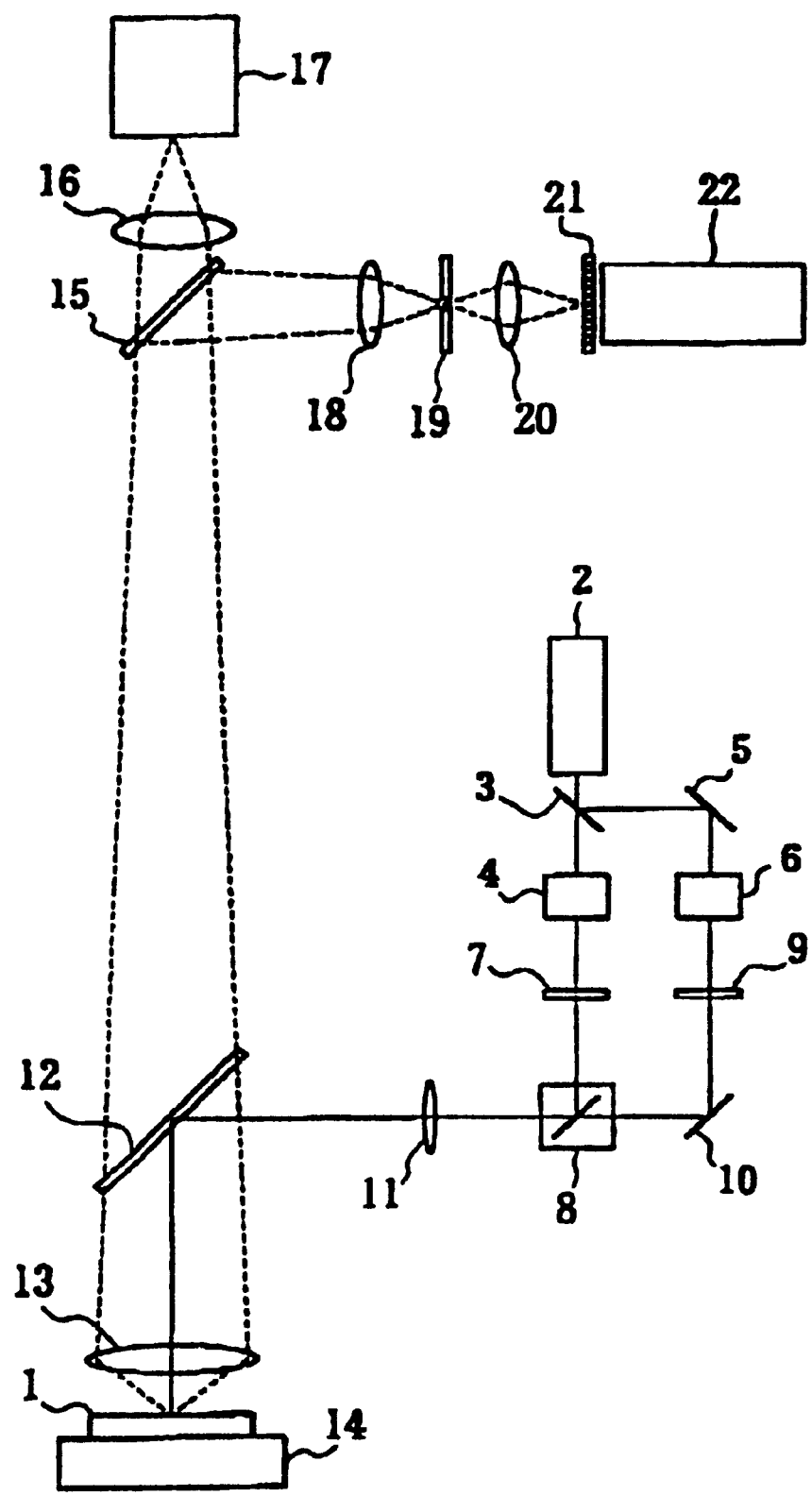
FIG. 5 is a drawing showing construction of a microscope according to a working embodiment of the present invention.
Figure 6:
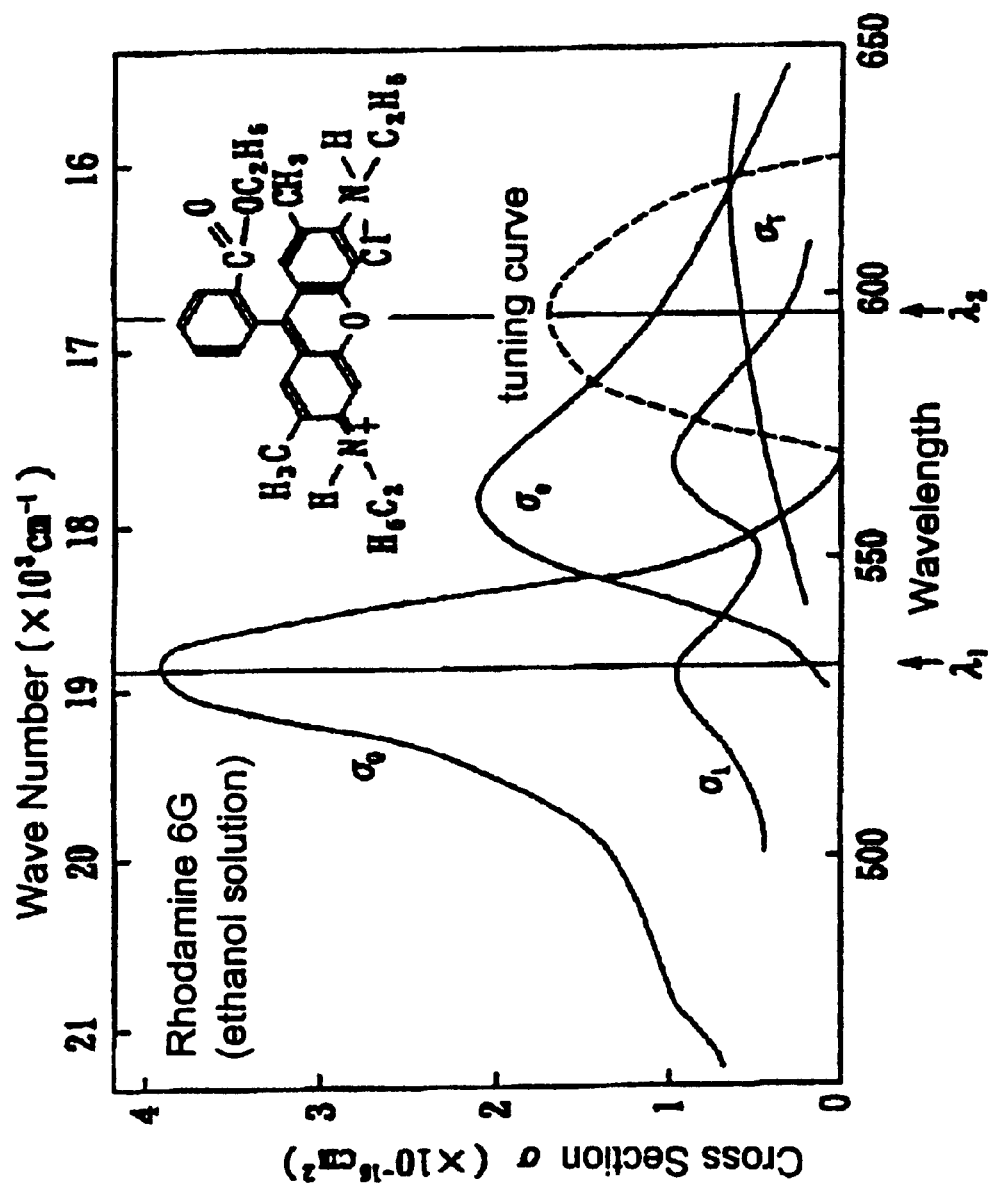
FIG. 6 is a characteristics diagram showing optical characteristics of the sample shown in FIG. 5.

FIG. 5 is a drawing showing construction of an example of a microscope. This working example observes a biological sample 1 that has been dyed by the fluorescent dye Rhodamine 6G. Rhodamine 6G has the optical characteristics shown in TABLE 1 and FIG. 6. A light source 2, comprising Nd:YAG laser medium, is a Nd:YAG picosecond laser that outputs laser light (fundamental wavelength= 1064 nm) at a pulse width of about 30 picoseconds. Laser light from this laser is frequency-doubled to obtain pump light at a wavelength of 532 nm. Light at a wavelength of 599 nm, corresponding to the wavelength of second-order Stokes' light converted by a Raman crystal, is used as erase light. For the present working example, pump light and erase light are respectively made to have double-partitioned 1×2 spatial modes, as shown in FIG. 1, and light is focused upon sample 1 so that pump light and erase light are made to partially overlap spatially.

TABLE 1

Approximate absorption cross sections during transitions between various energy levels of Rhodamine 6G

| | |
|---|---|
| $\sigma_0$ (cross-sectional area during transition from ground state to first electronic excited state) | $10^{-16}$ cm$^2$ (532 nm)(1) |
| $\sigma_1$ (cross-sectional area during transition from first electronic excited state to second electronic excited state) | $10^{-17}$ cm$^2$ (599 nm)(1) |
| $\lambda_f$ (fluorescence intensity maximum value wavelength) | 555 nm(1) |

(1)E. Sahar, et al., IEEE. J. Quantum Electronics, 13, 962 (1977).

Light emitted from the Nd:YAG picosecond laser 2 of FIG. 5 is split into two beams by a beam splitter 3. One of these beams is converted into a doubled beam of 532 nm wavelength as pump light by a KDP crystal 4. After reflection by a mirror 5, the other beam becomes erase light by conversion to a beam of 599 nm wavelength by a Raman shifter 6 formed from crystalline barium nitrate Ba(NO$_3$)$_2$.

Figure 7:
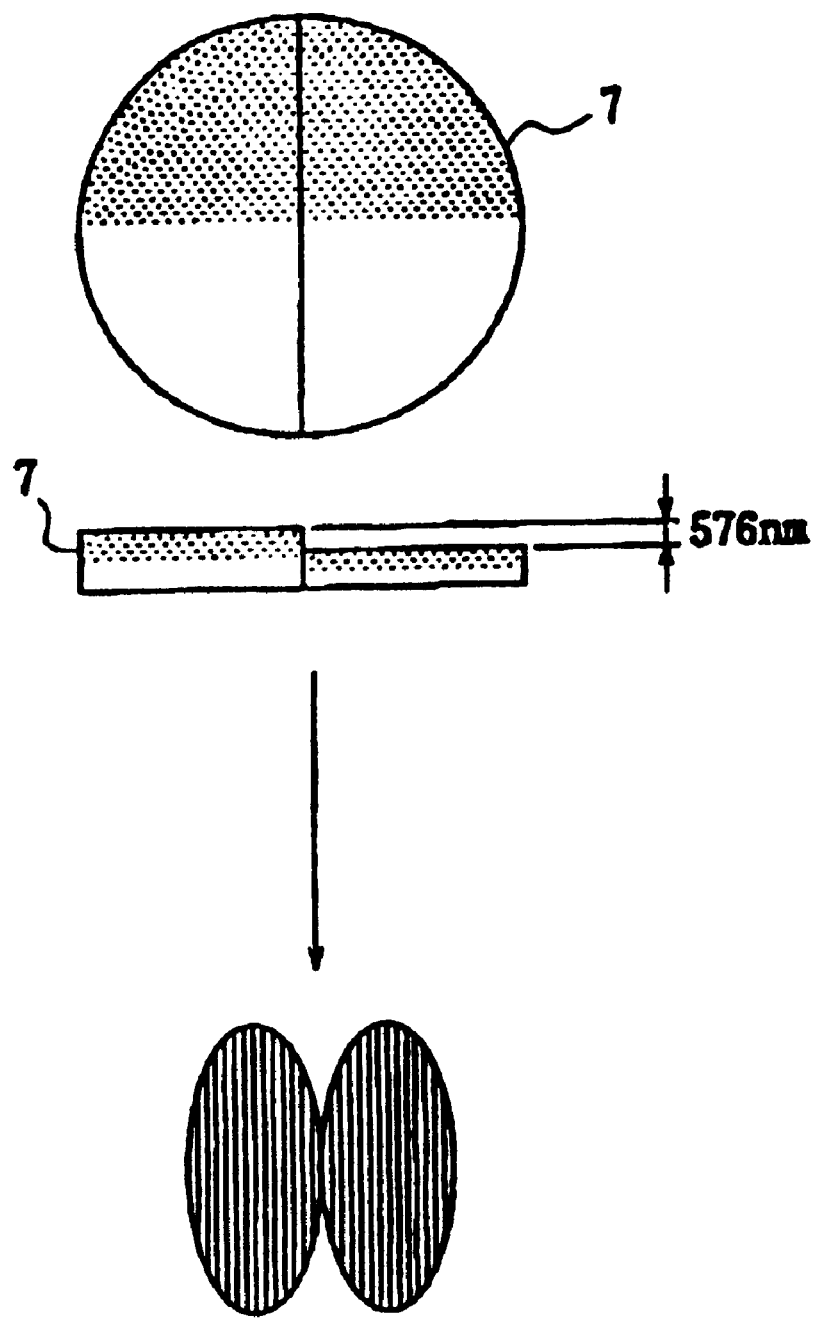
FIG. 7 is an explanatory drawing for explanation of the operation and construction of the phase plate for forming multiple modes of pump light in FIG. 5.

Pump light emitted from KDP crystal 4 is given 1×2 multiple spatial modes by passage through a phase plate 7, and then this beam enters a dichroic mirror 8. Phase plate 7, as shown in FIG. 7, is constructed so as to impart a phase differential of just n in two adjacent regions to the 532 nm wavelength pump light according to etching depth of an optically polished quartz glass substrate that has undergone chemical etching, thereby transforming erase light into a multi-spatial mode beam.

Figure 8:
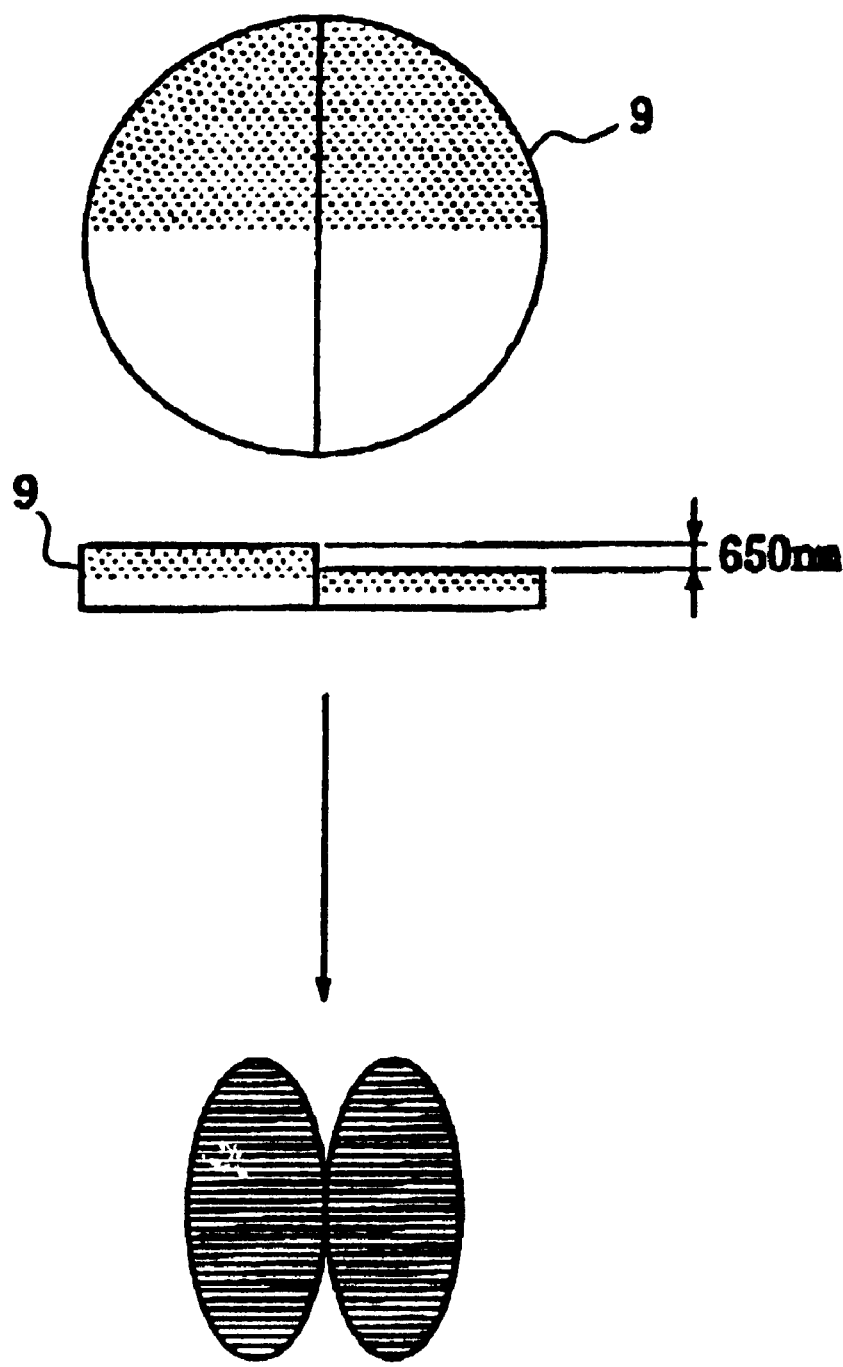
FIG. 8 in the same manner is an explanatory drawing for explanation of the operation and construction of the phase plate for forming multiple modes of erase light in FIG.5.
Figure 9:
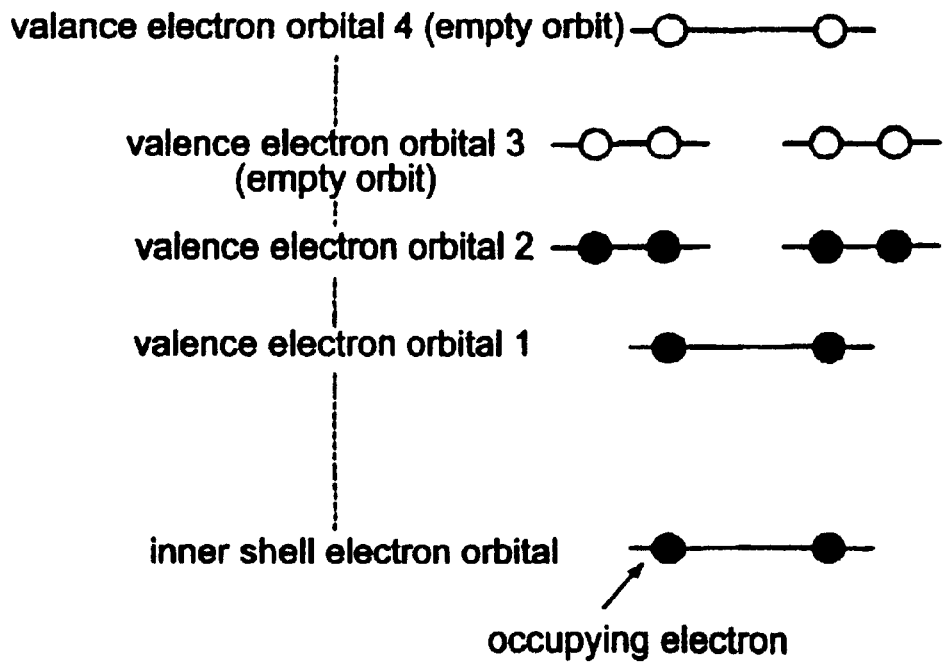
FIG. 9 is a conceptual drawing indicating electron structure of valence electron orbitals of a molecule comprising the sample.
Figure 10:
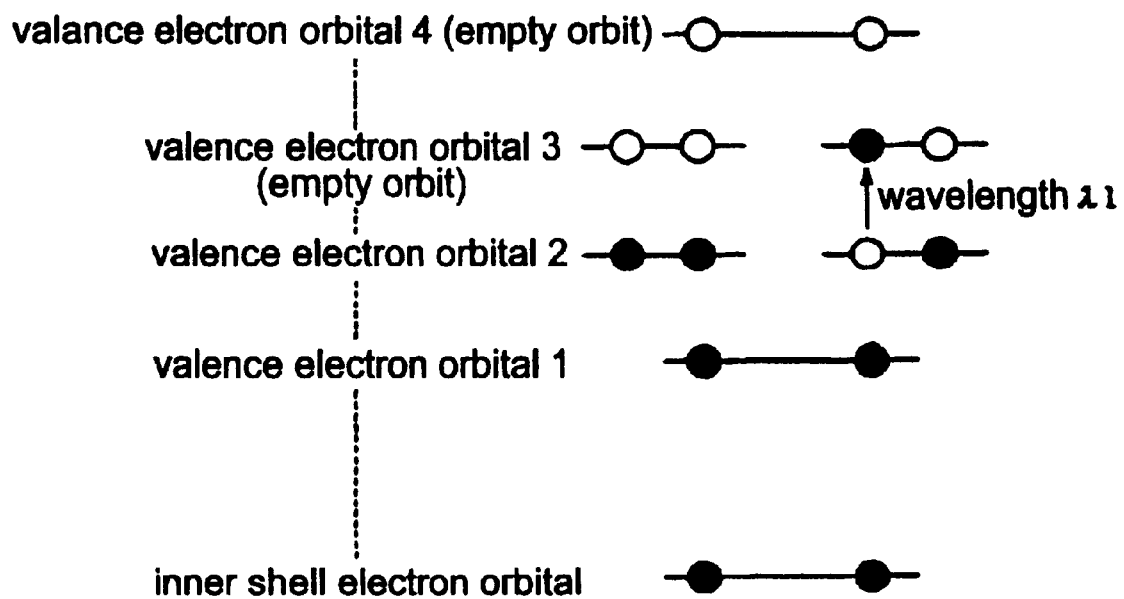
FIG. 10 is a conceptual drawing showing the first excited state of the molecule of FIG. 9.
Figure 11:
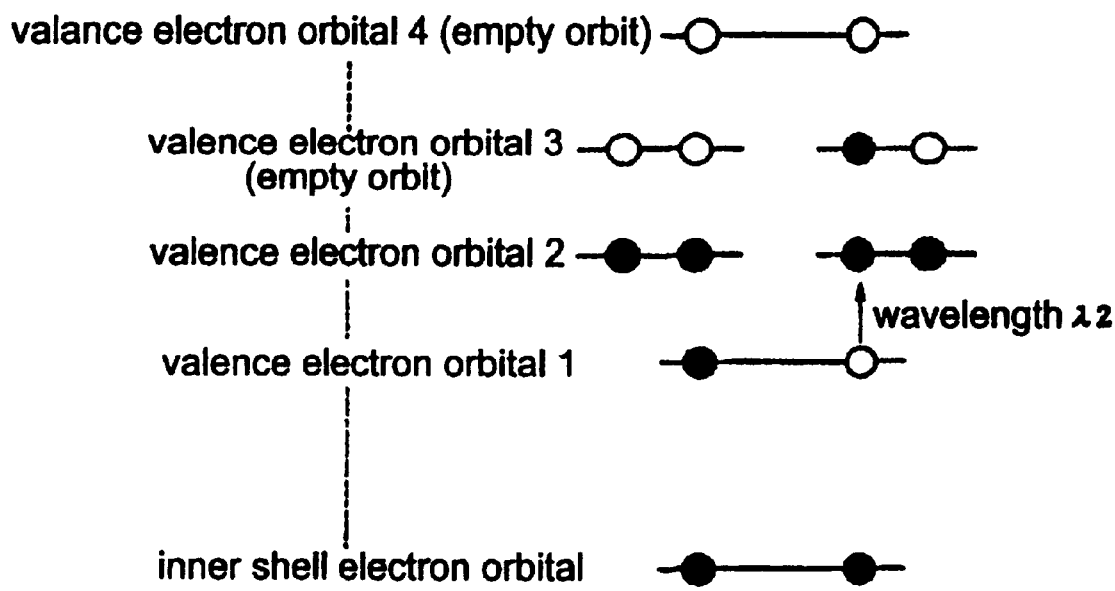
FIG. 11 in the same manner is a conceptual drawing showing the second excited state.
Figure 12:
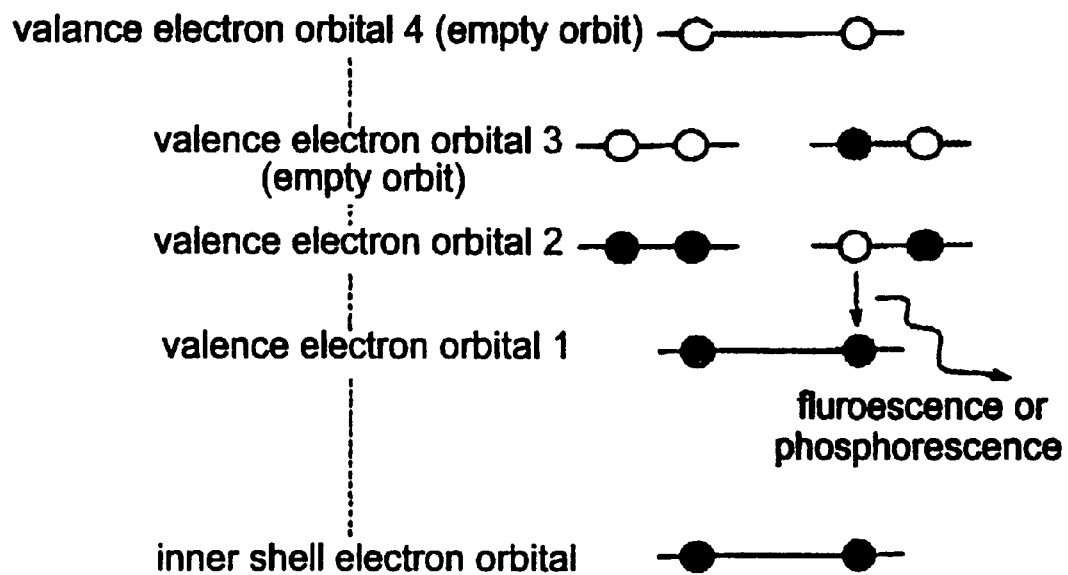
FIG. 12 in the same manner is a conceptual drawing showing conditions of return to the ground state from the second excited state.
Figure 13:
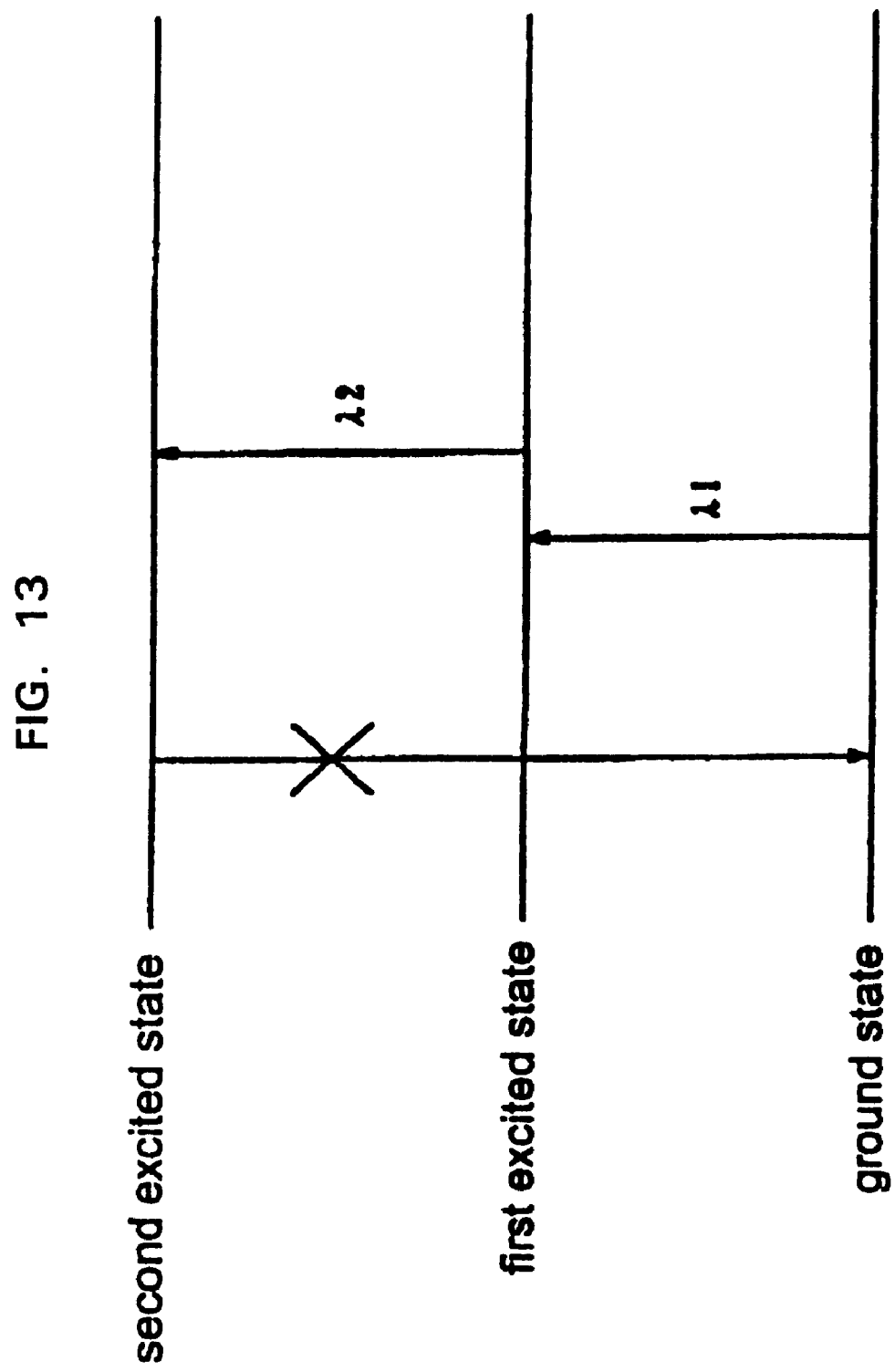
FIG. 13 is a conceptual drawing for explanation of the double-resonance absorption process occurring in a molecule.
Figure 14:
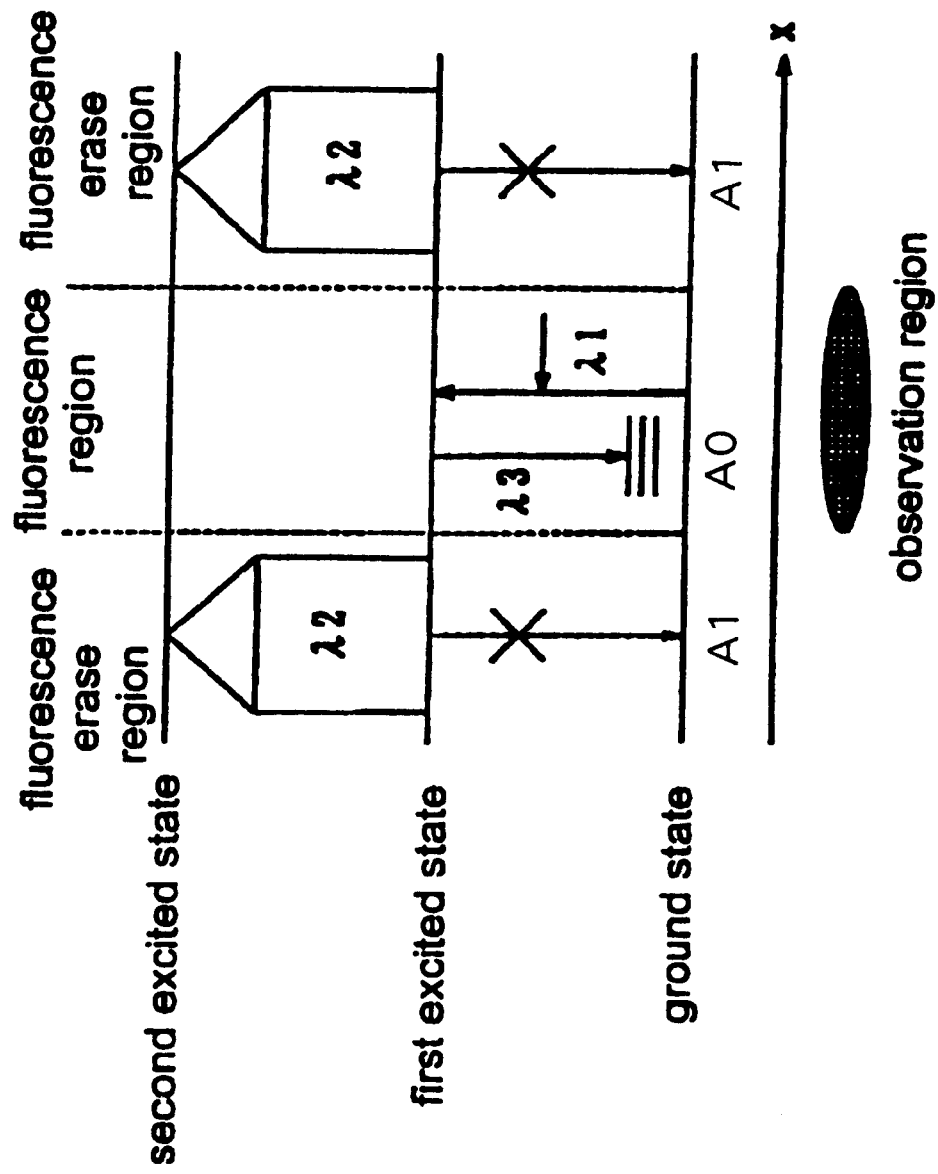
FIG. 14 in the same manner is a conceptual drawing for explanation of the double-resonance absorption process.
Figure 15:
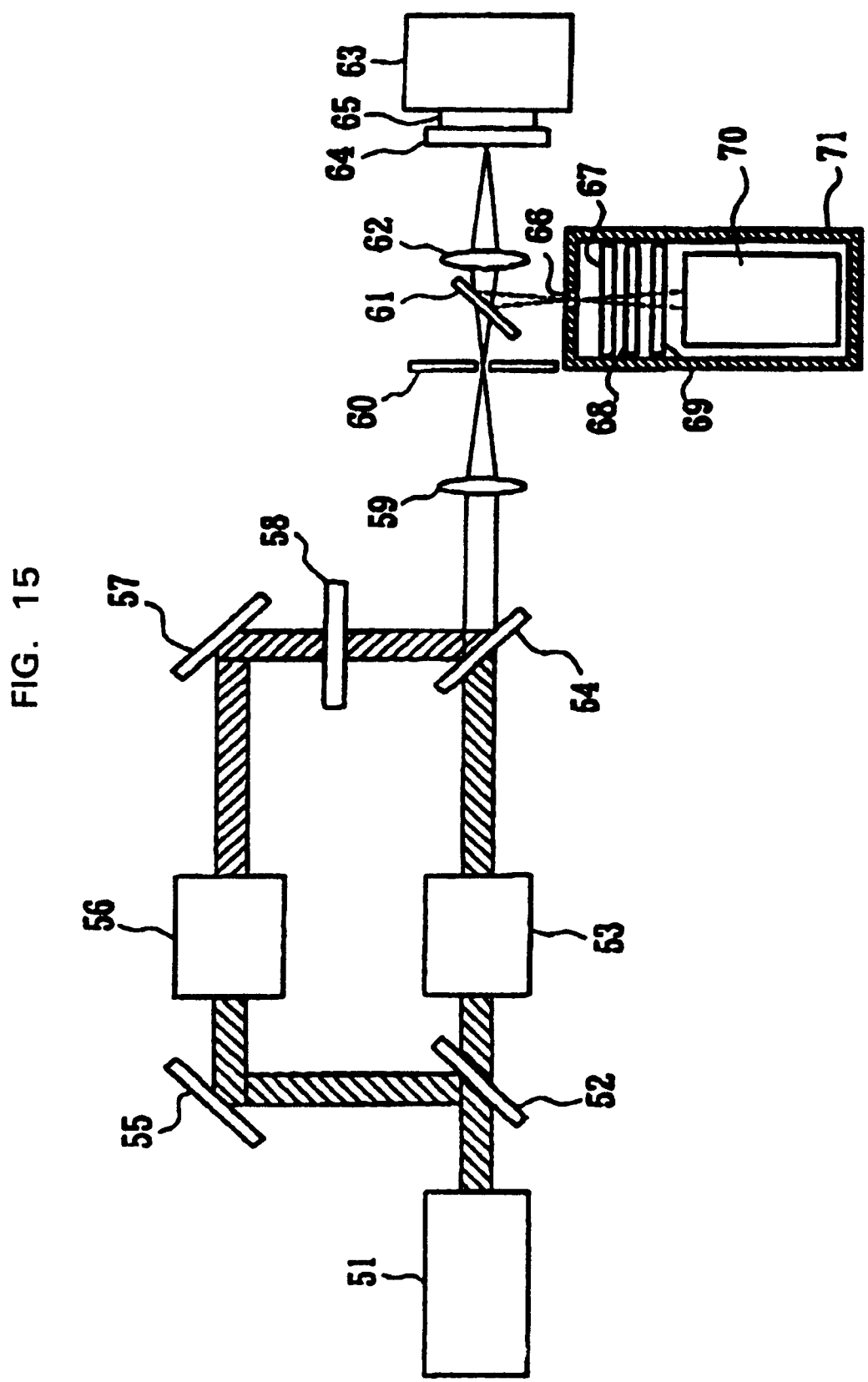
FIG. 15 is a structural drawing showing construction of an example of a super-resolution microscope proposed previously by the inventors of the present invention.
Figure 16:
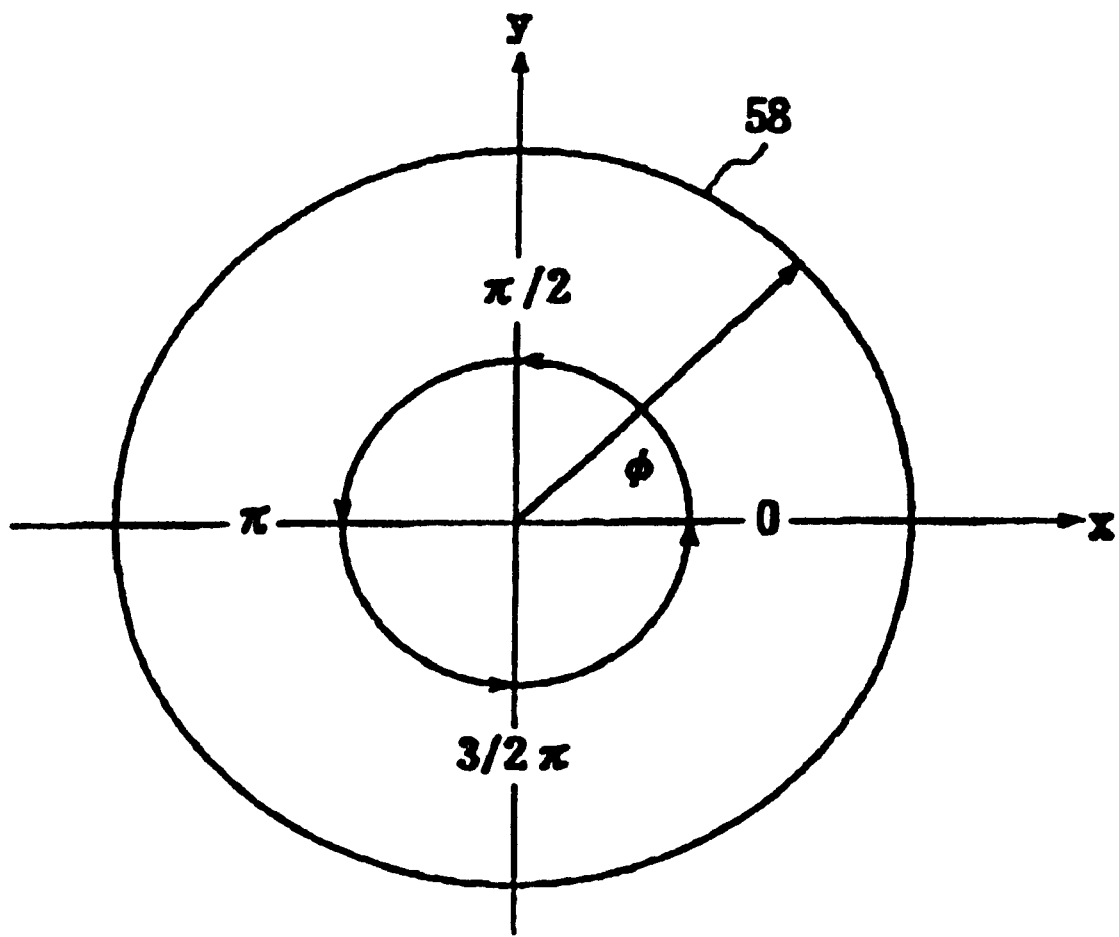
FIG. 16 is a top view showing construction of the phase plate shown in FIG. 15.
Figure 17:
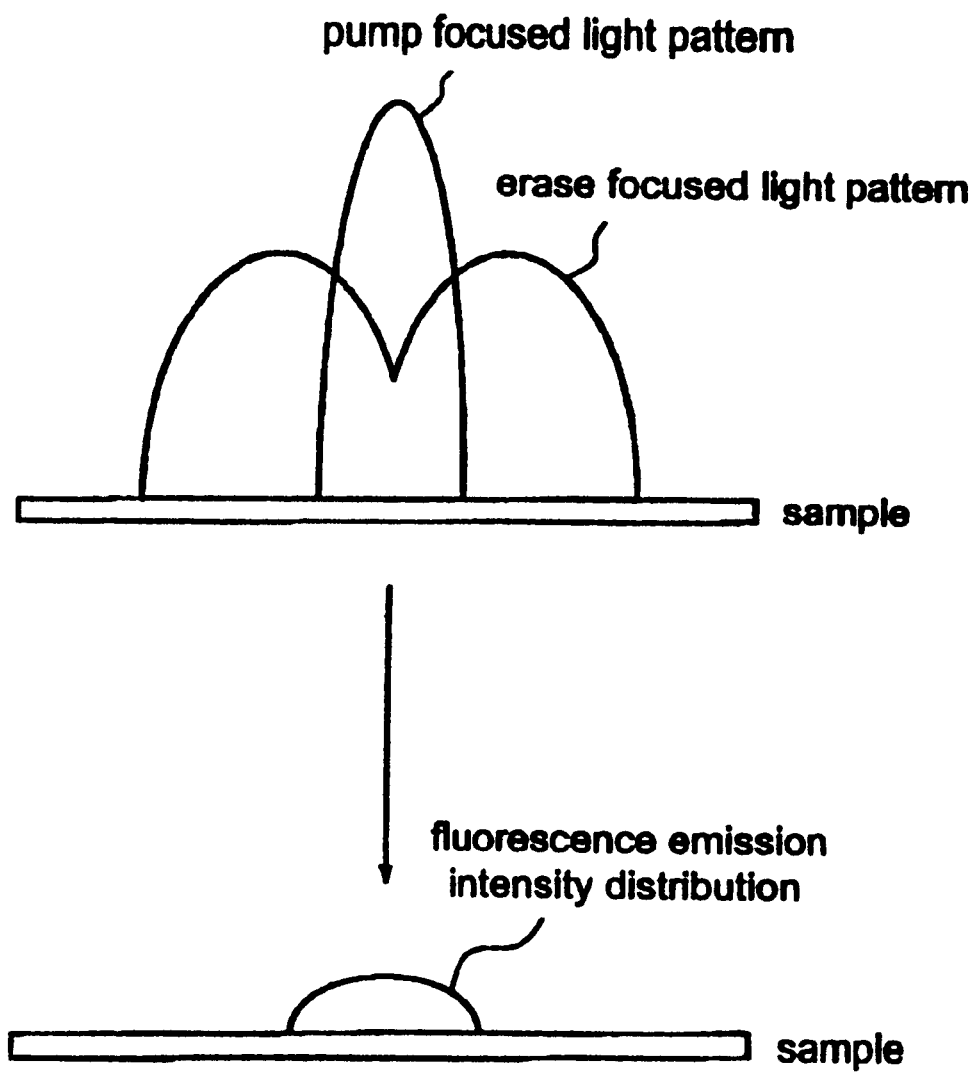
FIG. 17 is an explanatory-drawing for explanation of the points of improvement of the super-resolution microscope shown in FIG. 15.

In the same manner, erase light emitted from Raman shifter 6 is made to pass through phase plate 9, thereby being given 1×2 multiple spatial modes. This erase light then goes to a mirror 10 and then is made incident upon a dichroic mirror 8. A phase plate 9, as shown in FIG. 8, is constructed by chemical etching of an optically polished quartz glass substrate, in the same manner as phase plate 7, to adjust etching depth thereof to the erase light wavelength of 599 nm, thereby transforming erase light into a beam of multiple spatial modes.

The pump light and erase light are combined at dichroic mirror 8. This combined beam passes through a relay lens 11 and a half mirror 12 and then is focused upon a sample 1 carried upon a sample stage 14.

Here the pump light and erase light focused upon sample 1 have the phase relationship shown in FIG. 1. Half of the pump light, that has been given 1×2 multiple spatial modes, spatially overlaps the erase light. Fluorescence is suppressed in this overlapping part. This spatial overlap of pump light and erase light can be adjusted by dichroic mirror 8, mirror 10, and half mirror 12.

However, fluorescent light emitted from sample 1 is sent through an objective lens 13, a half mirror 12, and a half mirror 15, then is focused upon the imaging surface of a CCD camera 17 by a focus lens 16, thereby making the fluorescent image observable.

Moreover, that part of fluorescent light reflected by half mirror 15 is focused by a lens 18 at a pinhole 19 which is a spatial filter. Fluorescent light passing through this pinhole 19 passes through a lens 20 and a transmission-type diffraction grating 21 and then is focused upon the imaging surface of an ICCD camera 22.

Here ICCD camera 22 comprises a light-electron conversion film and a two-dimensional photoelectron amplification tube. Fluorescent light passes through transmission-type diffraction grating 21 and is imaged by ICCD camera 22 in the form of a fluorescence spectrum. Therefore while sample 1 undergoes two-dimensional scanning using sample stage 14, if a fluorescent signal is measured, data at each point are stored in memory of a personal computer, etc., and then if data are displayed on a CRT, etc. monitor, imaging is possible of the sample 1, which is the object.

According to the present working example of a microscope, since a region of fluorescent signal can be selected that is even somewhat more minute than the laser light focused upon sample 1, potential as a measurement method can be extremely high. Moreover, if a piezo element is used to drive sample stage 14, positional resolution can be greatly increased to 10 nm. Therefore the present working example can be made to have sufficient performance commensurate with the spatial resolution of a super-resolution microscope.

Furthermore, pinhole 19 of the microscope of the present working example is disposed confocally in the microscope optical system. Therefore three-dimensional observation of sample 1 is also possible. That is to say, since only fluorescent light generated from the focal point position of laser light can be transmitted, if the sample stage 14 is moved along the direction of the optical axis, and if laser light is scanned in two dimensions, it becomes possible to obtain transverse layer images of sample 1 along the optical depth direction.

Moreover, the above mentioned working example obtained pump light and erase light from output light from a single Nd:YAG picosecond laser 2. However, construction is also possible so as to obtain pump light and erase light from separate light sources.

What is claimed is:

1. A microscope for observation of a sample that is dyed by a molecule having at least three electron states including a ground state and characterized as having a first light source for generation of a first light of a wavelength λ1 which causes a transition of said molecule from the ground state to a first excited state, a second light source for generation of second light of a wavelength λ2 which causes a transition of said molecule from a first excited state to a second excited state of higher energy level, a condensed light optical system for focusing of said first light and second light upon said sample, and an emitted light detector for detection of light emitted from said molecule;

wherein the microscope is constructed such that light of said first light from said first light source is generated to form a multi-spatial mode condensation pattern and such that said condensed light optical system makes just a portion of the region of said condensed light pattern of the first light spatially overlap said condensed light pattern of the second light.

2. The microscope according to claim 1, wherein said first light source and second light source are coherent light sources.

3. The microscope according to claim 2, wherein the microscope has a phase distribution generation element that causes the wavefront of said first light of wavelength λ1 to have a phase distribution.

4. The microscope according to claim 3, wherein said phase distribution generation element has a multiplicity of divided regions for which the wavefront has a phase differential of either zero or π.

5. The microscope according to claim 4, wherein said divided region has a phase differential of π with respect to an adjacent region.

6. The microscope according to claim 1, wherein said second light also has a multi-spatial mode condensed light pattern.

7. The microscope according to claim 2, wherein said second light also has a multi-spatial mode condensed light pattern.

8. The microscope according to claim 3, wherein said second light also has a multi-spatial mode condensed light pattern.

9. The microscope according to claim 4, wherein said second light also has a multi-spatial mode condensed light pattern.

10. The microscope according to claim 5, wherein said second light also has a multi-spatial mode condensed light pattern.

* * * * *